US008747415B2

(12) United States Patent
Schafer

(10) Patent No.: US 8,747,415 B2
(45) Date of Patent: Jun. 10, 2014

(54) DEVICE AND METHOD FOR PERFORMING A FETAL PROCEDURE

(76) Inventor: Martin David Schafer, Beckwourth, CA (US)

(*) Notice: Subject to any disclaimer, the term of this patent is extended or adjusted under 35 U.S.C. 154(b) by 471 days.

(21) Appl. No.: 12/358,163

(22) Filed: Jan. 22, 2009

(65) Prior Publication Data

US 2010/0185209 A1 Jul. 22, 2010

(51) Int. Cl.
*A61B 17/42* (2006.01)

(52) U.S. Cl.
USPC .......................................................... 606/124

(58) Field of Classification Search
USPC ......................... 606/124, 126, 119, 122, 123; 119/712–849
See application file for complete search history.

(56) References Cited

U.S. PATENT DOCUMENTS

| | | | | |
|---|---|---|---|---|
| 666,463 | A | 1/1901 | Broadfoot | |
| 1,337,841 | A * | 4/1920 | Juhl | 606/124 |
| 1,690,942 | A | 11/1928 | Odell | |
| 1,934,513 | A | 11/1933 | Schulte | |
| 2,098,151 | A | 11/1937 | Junge | |
| 2,293,984 | A | 4/1942 | Kirschbaum | |
| 2,522,508 | A | 9/1950 | Frank | |
| 2,654,368 | A | 10/1953 | Matteson, Jr | |
| 2,668,528 | A | 2/1954 | Frick | |
| 2,737,182 | A | 3/1956 | Willman | |
| 2,774,353 | A | 12/1956 | Quist | |
| 2,791,219 | A | 5/1957 | Bowie | |
| 3,113,571 | A | 12/1963 | Jeeninga | |
| 3,183,911 | A | 5/1965 | Anglemyer | |
| 3,643,664 | A | 2/1972 | McMillan | |
| 3,868,958 | A | 3/1975 | Rarick | |
| 3,955,582 | A | 5/1976 | Pierce | |
| 4,502,486 | A | 3/1985 | Weiland | |
| 4,872,457 | A | 10/1989 | Thompson | |
| 5,573,539 | A | 11/1996 | Alexander | |

(Continued)

FOREIGN PATENT DOCUMENTS

| | | | |
|---|---|---|---|
| FR | 2505648 * | 11/1982 | A61D 1/08 |
| GB | 2029234 A * | 3/1980 | A61D 1/08 |
| GB | 2163654 | 5/1986 | |
| WO | WO 8606615 A1 * | 11/1986 | A61D 1/08 |

OTHER PUBLICATIONS

David E Noakes, Timoty J Parkinson, Gary C W England, Arthur's Veterinary Reproduction and Obstetrics, Eighth Edition, pp. 266-270, 282-289, 294.*

(Continued)

*Primary Examiner* — S. Thomas Hughes
*Assistant Examiner* — Anh Dang
(74) *Attorney, Agent, or Firm* — Ian Burns; ATIP Law

(57) ABSTRACT

A device for performing fetotomy on a dead fetus or repositioning of a live fetus has a primary attachment in the form of a looped brace that is provided around a fetal limb within the birth canal of the mother animal and engages the armpit or groin of the fetus. An extension bar connects the brace to a tensioning device. A secondary attachment such as a cable or chain is attached at the foot of the fetal limb and connected to the tensioning device. The tensioning device is operated to provide tension between the brace and the secondary attachment, thereby placing the fetal limb in traction. Sufficient traction causes removal of the entire limb without exposing sharp bone edges. Variations of the device may be used for a fetal repositioning procedure.

6 Claims, 7 Drawing Sheets

(56) References Cited

U.S. PATENT DOCUMENTS

| | | | |
|---|---|---|---|
| 5,910,146 | A | 6/1999 | Alexander |
| 6,355,047 | B1 | 3/2002 | Wallace |
| 6,409,738 | B2 | 6/2002 | Callicrate |
| 2005/0203334 | A1 | 9/2005 | Lonkey et al. |

OTHER PUBLICATIONS

Prof. Dr. M. El Naagar. Dr. Abdel-Razek, A.Kh, Dr. Ala' ELDin Zain Mahmoud, Ahmed Ali, Dr. Shehata Hassan Mohamed, Professor of Theriogenology, Faculty of Veterinary Medicine, Course of Obstetrics (Practical). pp. 27-37. Mar. 22, 2011. <http://www.evet.aun.edu.eg/p.p/Obstetrics_Practical.pdf>.*

Frazer, G.S. "Fetotomy Technique in the Mare." vol. 13, Issue 3, pp. 151-159. Equine Veterinary Education. 13 (3) 151-159. Jan. 5, 2010. <http://www.evj.co.uk/archive/downloads/EVE01_13_151_159.pdf>.*

Bovine Obstetrics Images. Sep. 4, 2006. <www.vet.ksu.edu/media/images/therio/bov_ob/index.htm>.*

GB 2 163 654 A (Martin Keith) Mar. 5, 1986 p. 1 line 99 p. 2 line 12 Figures 1, 2 Relevant to claim 9-18.

US 2 791 219 A (Bowie Maraine C) May 7, 1957 col. 1 line 65—col. 3 line 44 figures 1-3 Relevant to claims 9-12 14-18.

US 1 337 841 A (Juhl Peter C) Apr. 20, 1920 p. 1 line 47 p. 2 line 7 figures 1,2.

US 2 774 353 A (Quist Harvey L) Dec. 18, 1956 col. 1 line 41 col. 2 line 28 figures 1, 2.

* cited by examiner

DEVICE AND METHOD FOR PERFORMING A FETAL PROCEDURE

FIELD OF THE INVENTION

The present invention relates to fetal procedures, particularly fetotomy and more particularly to a method and device for removing the limbs of a deceased fetus. The invention also relates to fetal repositioning procedures.

BACKGROUND

The birthing of animals, including humans and livestock, has presented substantial problems for doctors, farmers and veterinary doctors for many years. The problem has been most severe in the cattle industry where current trends in genetic selection commonly cause calves to be born at a larger size. Cattle giving birth at 24 months or younger are particularly at risk of having birthing difficulty because their birth canal has not yet reached full adult size. Not uncommonly, a veterinary doctor or livestock handler will be faced with a serious problem when a fetus has died during the birthing process and is incorrectly positioned or physically too large to be delivered. If the dead fetus is not delivered promptly, infection and shock can cause death to the mother. Conventional devices to extract the entire fetus by pulling on the fetus while pushing against the hindquarters of the mother can be dangerous because extreme traction often causes fatal injury to the uterus and birth canal. A costly caesarian operation has the often fatal risk of infection due to the delivery of a rotting fetus through a surgical incision. An area of veterinary obstetrics called fetotomy has been developed to provide an alternative delivery technique. Fetotomy pertains to separating the fetus into parts and removing the fetus through the birth canal one piece at a time. Special knives and wire saws are typically used to perform this procedure. Wire saws present problems due to the extreme difficulty of passing a rough wire around fetal structures in a very confined space without injury to the mother animal. In addition, once the cuts are made, sharp surfaces of cut bones may be exposed to the delicate structures of the uterus and birth canal.

SUMMARY OF ONE EMBODIMENT OF THE INVENTION

Advantages of One or More Embodiments of the Present Invention

The various embodiments of the present invention may, but do not necessarily, achieve one or more of the following advantages:

the ability to fully remove limbs from a fetus with minimal cutting;

provide a method and device for removing fetal limbs without cutting the bones of the limb;

provide reduced risk of injury to the mother;

provide a method and device for fetotomy where the tractional forces are placed entirely on the dead fetus; and provide a method and device for repositioning of a fetus within the uterus or birth canal.

These and other advantages may be realized by reference to the remaining portions of the specification, claims, and abstract.

Brief Description of One Embodiment of the Present Invention

In an embodiment of the invention there is provided a method for performing fetotomy. The method provides a brace around a first portion of a fetal limb of a fetus and an attachment at a second portion of the fetal limb. Tension is provided to the fetal limb between the first and second portions sufficient to separate the fetal limb from the fetus.

In an embodiment of the invention there is provided a device for performing a fetotomy comprising a brace that engages a first portion of a fetal limb of a fetus and an attachment that engages a second portion of the fetal limb. A traction device applies relative traction between the brace and the attachment to cause the limb to separate from the fetus between the brace and the attachment.

In an embodiment of the invention there is provided a device for performing fetotomy comprising a brace and an extension bar extending from the brace. The brace comprises a rigid loop configured to pass around a fetal limb and engage a fetus at the base of the fetal limb.

In an embodiment of the invention there is provided a method for performing fetal repositioning. In a first step, a fetal repositioning device is provided into a birth canal of a mother animal. The fetal repositioning device comprises a brace, an extension piece extending from the brace and a handle at an opposite end of the extension piece from the brace. The brace is located at the base of the fetal limb of a fetus within the birth canal to maintain tension on the fetal limb and the handle is used to manipulate the fetus with the brace. In another embodiment, a secondary attachment is attached between the handle and the fetal limb to provide additional tension on the fetal limb, thus providing more efficient rotation and manipulation of the entire fetus compared to previous methods.

The above description sets forth, rather broadly, a summary of one embodiment of the present invention so that the detailed description that follows may be better understood and contributions of the present invention to the art may be better appreciated. Some of the embodiments of the present invention may not include all of the features or characteristics listed in the above summary. There are, of course, additional features of the invention that will be described below and will form the subject matter of claims. In this respect, before explaining at least one particular embodiment of the invention in detail, it is to be understood that the invention is not limited in its application to the details of the construction and to the arrangement of the components set forth in the following description or as illustrated in the drawings. The invention is capable of other embodiments and of being practiced and carried out in various ways. Also, it is to be understood that the phraseology and terminology employed herein are for the purpose of description and should not be regarded as limiting.

DESCRIPTION OF CERTAIN EMBODIMENTS OF THE PRESENT INVENTION

In the following detailed description of the particular embodiments, reference is made to the accompanying drawings, which form a part of this application. The drawings show, by way of illustration, specific embodiments in which the invention may be practiced. It is to be understood that other embodiments may be utilized and structural changes may be made without departing from the scope of the present invention.

Figure 1:
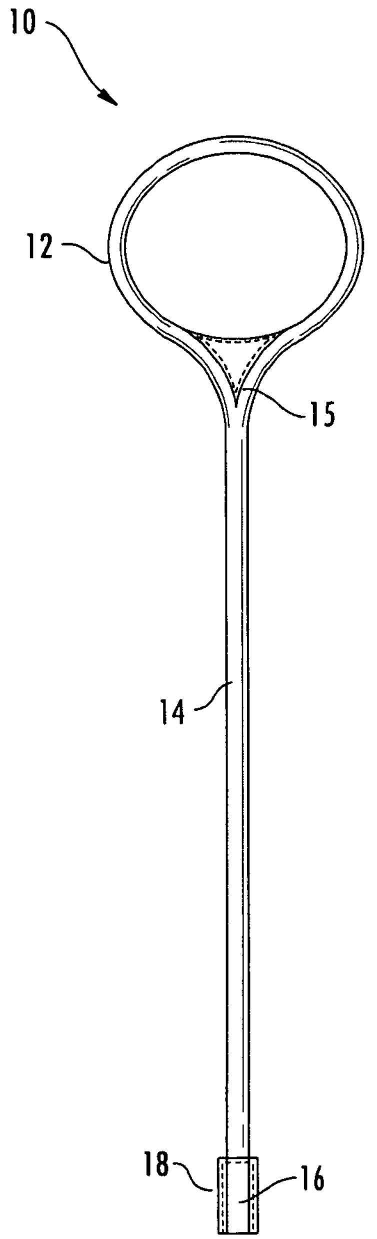
FIG. 1 is substantially a plan view of one embodiment of a fetotomy device of the present invention.
Figure 2:
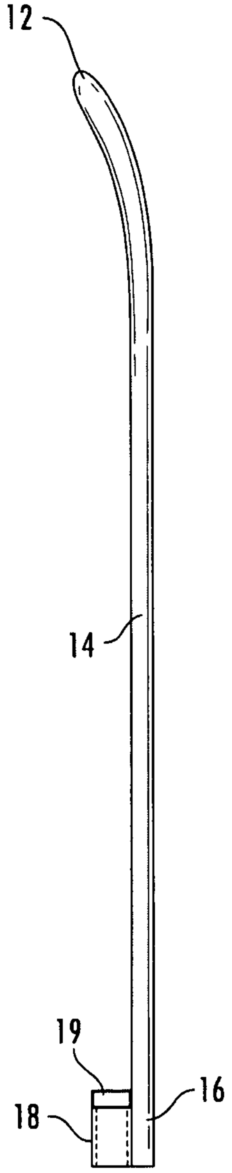
FIG. 2 is substantially a side view of the fetotomy device of FIG. 1.

In FIG. 1, there is shown a device 10 for performing a fetotomy procedure in accordance with an embodiment of the invention. A side view of the device 10 is shown in FIG. 2. For the purpose of the illustration, the device 10 will be shown and described with sizes suitable for performing fetotomy and fetal repositioning on a calf fetus. However, as will be apparent to a person skilled in the art, modifications may be made to the device 10 to make the device 10 suitable for performing fetotomy and/or fetal repositioning on other mammals, including humans.

The device 10 includes a brace 12 which may be a circle, oval or other looped shape of a suitable material. In one embodiment, the brace 12 is a loop of ½ inch (12 mm) stainless steel approximately 6 inches (150 mm) in diameter, though other materials and dimensions may be used. The device 10 further includes an extension bar 14 to which the brace 12 is secured at a first end 15. The brace 12 may be fitted to the extension bar in a secure manner such as by welding or by attachment mechanisms such as rivets, bolts, and similar attachment devices. Alternatively, the brace 12 and extension bar 14 may be integrally formed, such as by cutting from solid material or by casting. In one embodiment, the extension bar may be a ½ inch (12 mm) stainless steel square or round rod, though other materials and dimensions may be used. The extension bar 14 may be of a material that can withstand extreme compressive force of the type that will be described below. The length of the extension bar 14 may be any suitable length such as to locate a tensioning device, described below, outside of the birth canal. In one embodiment, the length of the extension bar is at least the length of a fetal limb. In one embodiment the length of the extension bar is approximately 19 inches (475 mm) such that the extension bar 14 and brace 12 together have a combined length of approximately 25 inches (625 mm).

Figure 3:
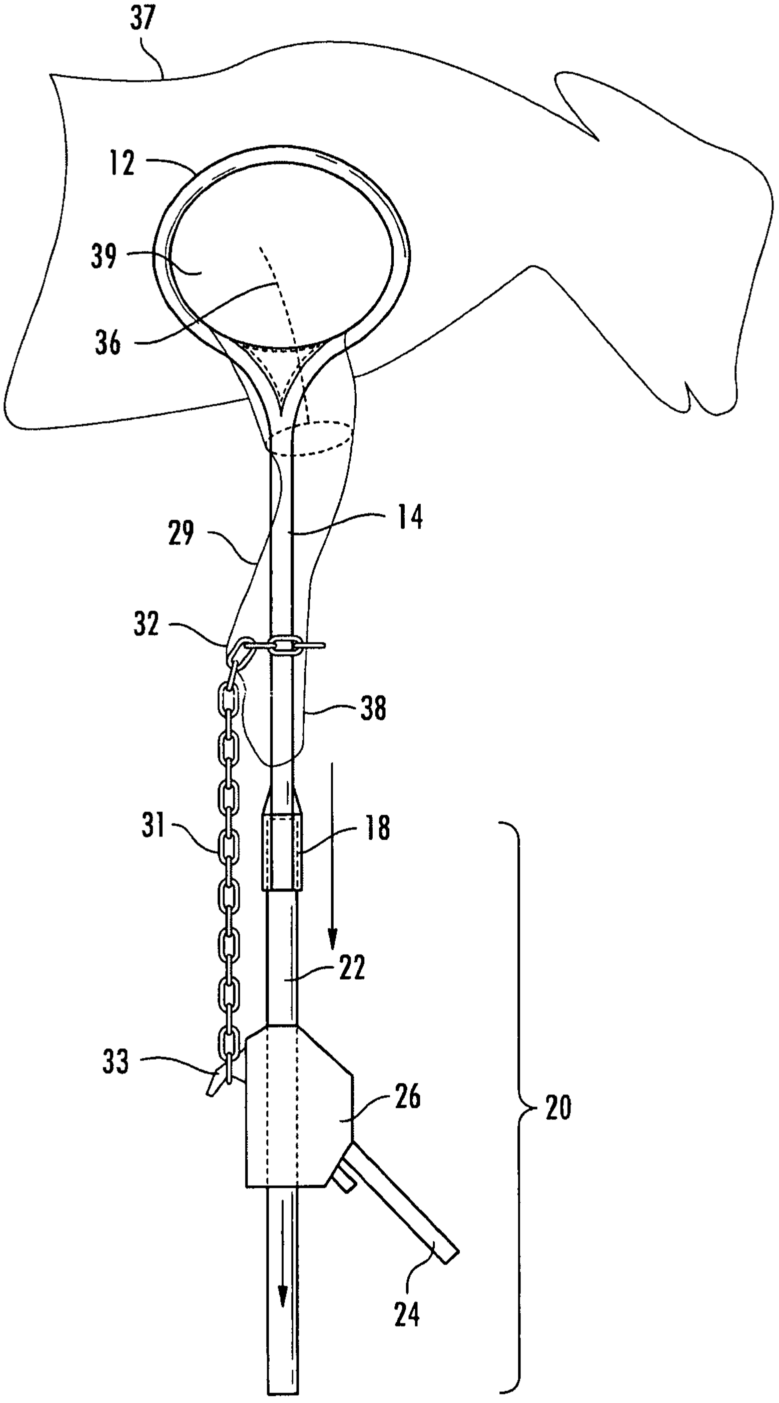
FIG. 3 substantially illustrates attachment of the fetotomy device of FIGS. 1 and 2 to a fetal limb.

At an opposite end 16 of the extension bar 14, there is provided a coupler 18 for engagement with a tensioning or traction device 20. One such tensioning device, illustrated in FIG. 3, provides a bar 22 and a friction jack 26 such as produced by Keysco Tools, Cleveland Ohio. The coupler 18 provides a sleeve approximately 2½ inches (50 mm) long, having a 1 inch (25 mm) internal diameter with a cap 19 (FIG. 2) received on an end of the sleeve. The coupler 18 receives the bar 22. Operation of the handle 24 of the friction jack 26 causes the friction jack to move along the bar 22.

Figure 4:
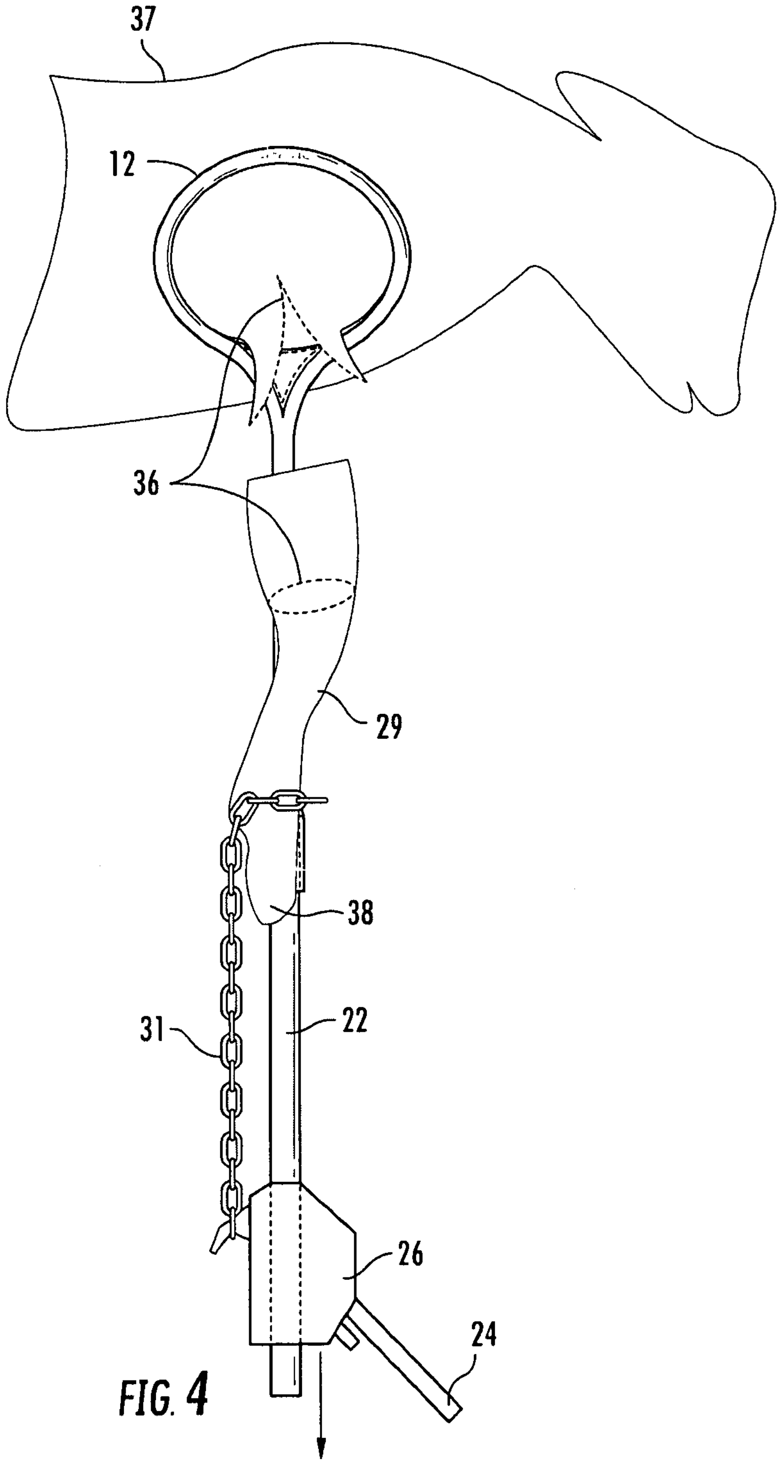
FIG. 4 substantially illustrates removal of the fetal limb.
Figure 5:
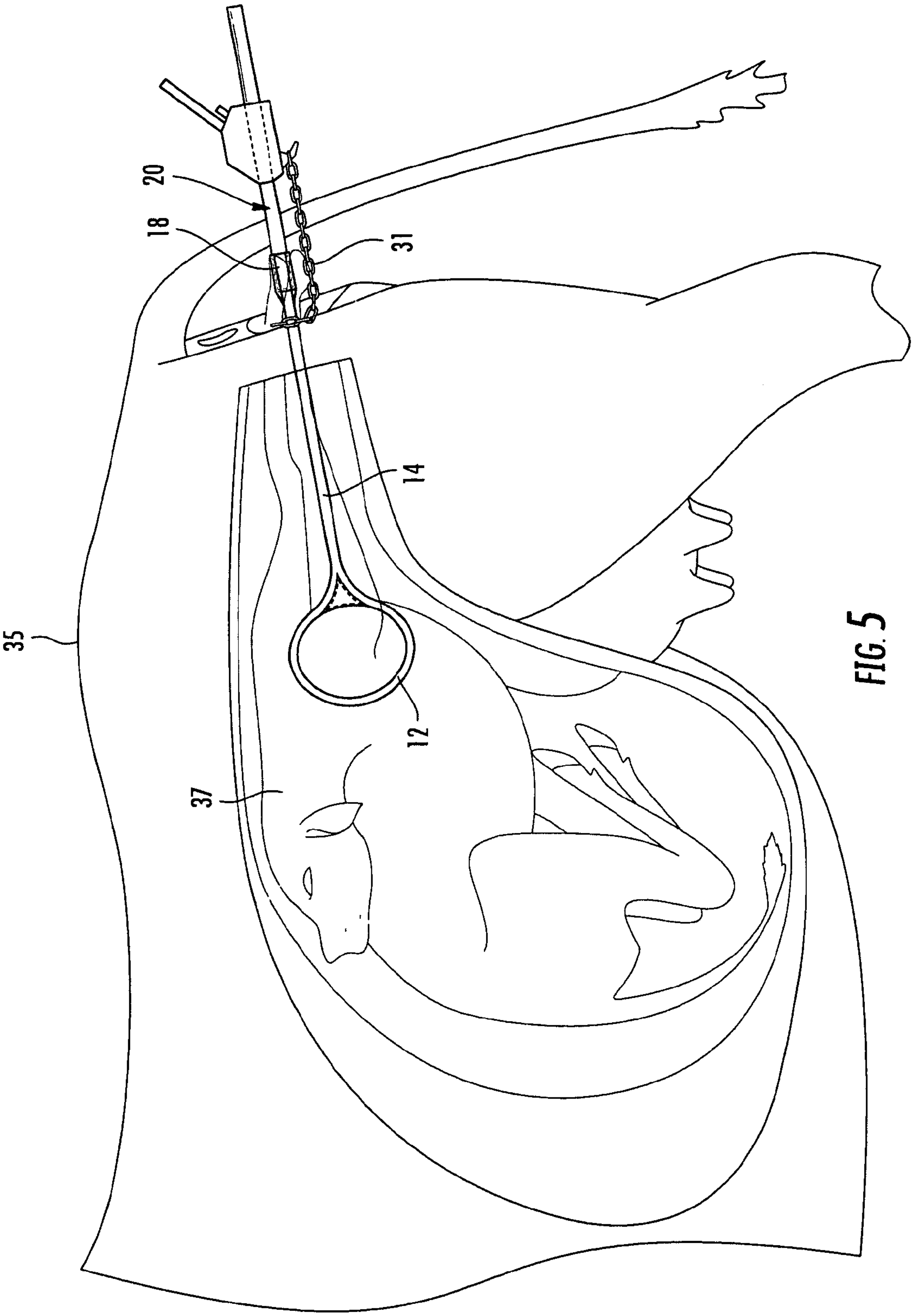
FIG. 5 substantially illustrates engagement of a fetotomy device with a fetus within a mother animal.
Figure 6:
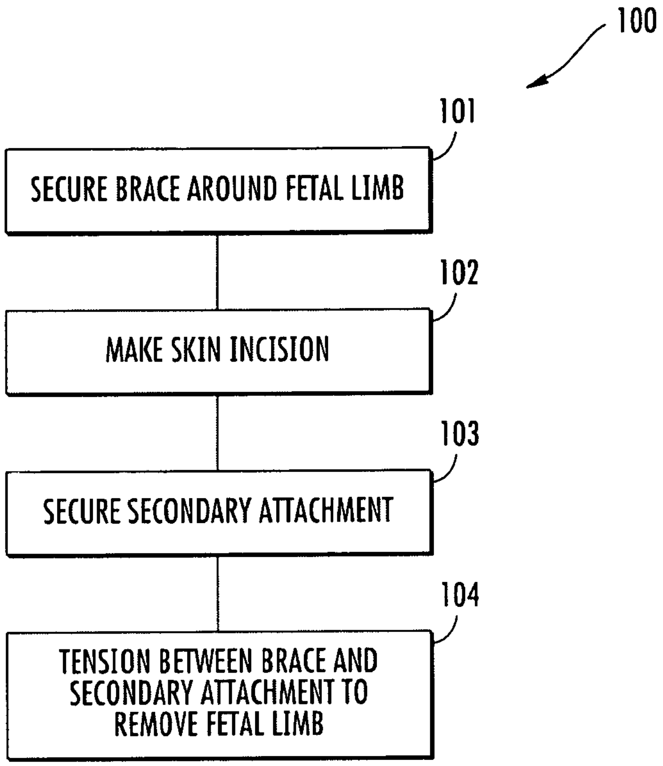
FIG. 6 substantially illustrates a flowchart of a fetotomy method.

A method for performing a fetotomy using the device 10 will now be described with reference to FIGS. 1 to 5 and to the flowchart 100 depicted in FIG. 6. At step 101, the device 10 is inserted along the fetal limb 29 of a fetus 37 which is inside the uterus or birth canal of the mother animal 35 (FIG. 5). Details of the mother animal 35 are omitted from FIGS. 3 and 4 for clarity. The device 10 is inserted with the brace 12 around the fetal limb 29 and slid along the fetal limb 29, until the brace 12 engages the base 39 of the fetal limb, i.e. either the armpit or groin. The device 10 and particularly the brace 12 provides a primary attachment. The extension bar 14 of the device 10 is connected to the tensioning device 20, located outside of the mother animal 35, via the coupler 18. At step 102, a skin incision, described in greater detail below, is optionally made in the fetal limb. At step 103, a secondary attachment device 31 is attached between a second portion of the fetal limb 29 and the tensioning device 20. In one embodiment, one end 32 of the secondary attachment device 31 is attached to the fetal foot 38 and the other end 33 is attached to the friction jack 26 of the tensioning device 20, which may include a hook or similar attachment for receiving the secondary attachment device 31. The secondary attachment device 31 may be a common calf chain, cable, chain, rope or similar elongate attachment. The secondary attachment device 31 may be flexible or rigid.

The handle 24 of the friction jack 26 is then operated to move the friction jack 26 along the bar 22 in the direction away from the brace 12. As the tensioning device 20 is operated, tension is placed on the secondary attachment device 31 while the extension bar 14 and brace 12 are rigid and remain fixed. Once the secondary attachment device is tensioned, further operation (step 104) of the tensioning device 20 will pull on the foot through the secondary attachment 31 while pushing at the base 39 of the limb with the brace 12. The effect is to cause traction of the fetal limb 29 between the brace 12 and the point of attachment of the secondary attachment device 31, e.g. the fetal foot 38. When sufficient tension is applied, the fetal limb 29 will tear away from the fetal body 37, as shown in FIG. 4.

The result is an extraction of the fetal limb(s) and associated muscle groups with the absence of sharp bone fragments. Because there are no stumps left, the doctor or livestock handler is provided with more room to manipulate the remainder of the dead fetus into the correct (head-forward) position in order to make delivery of the remaining portion of the fetus easier. In addition, the remaining portion of the fetus is narrower at the shoulders and/or the hips, further simplifying the delivery. Further manipulation of the dead fetus may include the removal of additional fetal limbs using the device 10 in the manner described above. As shown in FIG. 2, the brace 12 has a curvature that facilitates better engagement and purchase on the body of the fetus. The shape and configuration of the loop will be dependent on the species of animal on which the device 10 is intended to be used.

In one embodiment, an incision 36 (FIG. 3) may be made in the skin of the fetus between the brace 12 and the secondary attachment 31. In one embodiment, the incision is made circumferentially around the long axis of the fetal limb at a location on the limb between the primary and secondary attachments. The incision 36 has the effect of releasing the skin and allowing the limb to be more easily removed. In one embodiment, the incision is made at the level of the elbow. In one embodiment, the incising blade is inserted as little as possible into the birth canal in order to minimize the risk of harm to the mother.

An advantage of using the device 10 in the method described above is that the forces involved are entirely on the dead fetus. That is, the brace pushes against the base of the fetal limb while the secondary attachment device pulls on the fetal foot, or more toward the base of the fetal limb if required. Thus no forces are exerted on the mother.

A further advantage is that no bones are cut and thus no bone cutting implements are required to be inserted into the birth canal. The only incision that is required, in some embodiments, is the release of the skin of the fetal limb. The method described above allows the entire front limb to be removed, including the shoulder blade. Similarly, the rear leg will separate at the hip joint, leaving no sharp edges.

While the embodiments describe the tensioning device with specific reference to a friction jack, alternative tensioning devices may be used provided they are adapted to apply sufficient tensioning forces between the device 10 and the secondary attachment 31. Alternative tensioning devices include other forms of friction jack, as well as a cable winch, pulley, ratchet system, hydraulic pump, electrical motor or lever.

Figure 7:
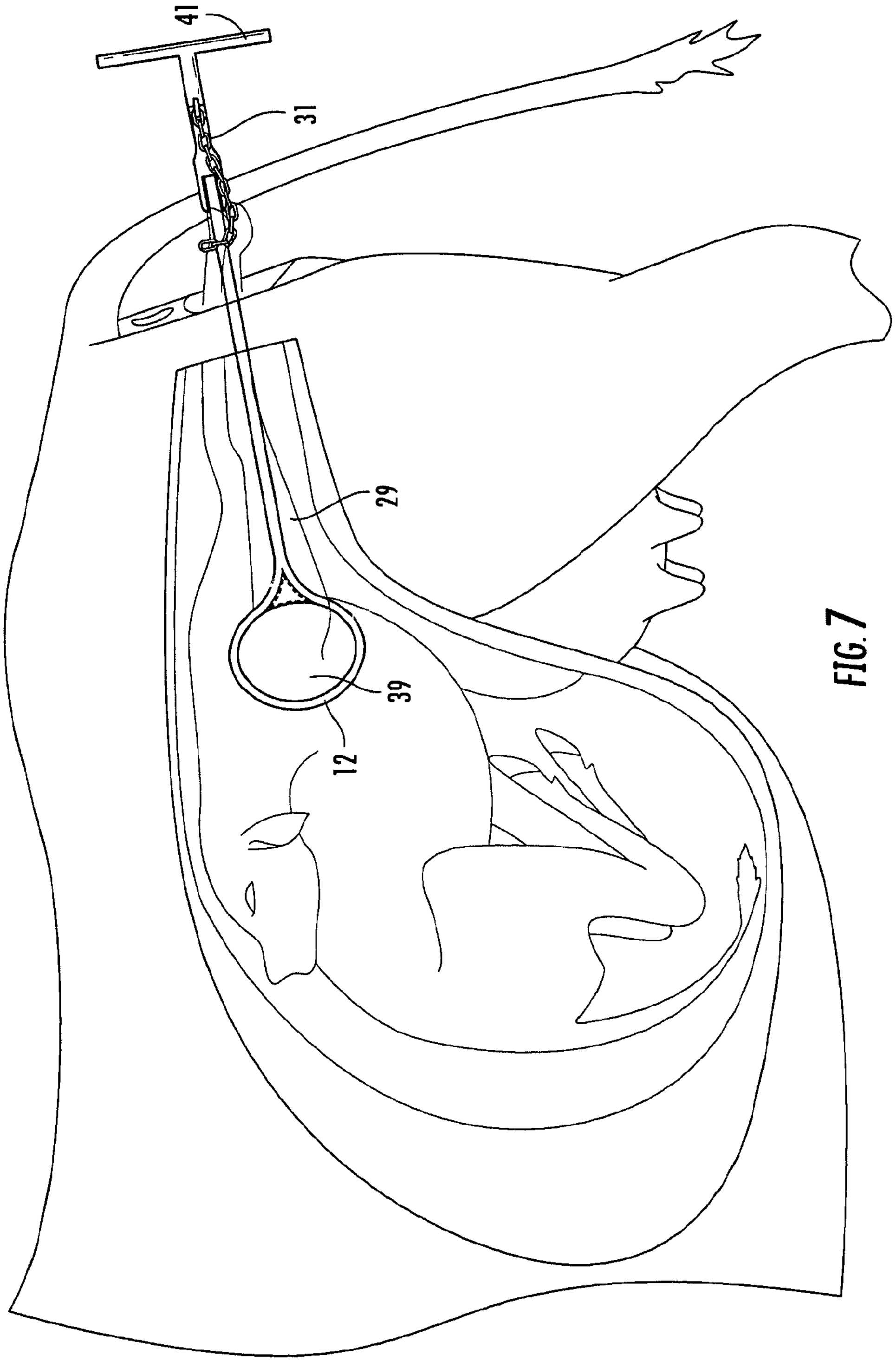
FIG. 7 substantially illustrates a method of fetal repositioning using an alternative configuration of a fetotomy device.

In an alternative embodiment illustrated in FIG. 7, the device 10 (shown in detail in FIG. 1) may be provided with a handle 41 in place of the tensioning device. The handle 41 may be provided via a coupler (similar to that shown in FIG. 1 as coupler 18) or otherwise connected to the device 10. The handle 41 is depicted as a T-shape, though a person skilled in the art will readily understand that other shaped handles may be used. In this configuration, the device 10 may be used as a fetal repositioner. The brace 12 is located, as described above, around a fetal limb 29 and positioned at the base 39 of the fetal limb. In addition, the fetal limb 29 is typically attached to the handle 41, by a chain or similar flexible or rigid secondary attachment 31. The handle 41 may then be used to manipulate the fetus, such as by pushing, pulling, rotating etc in order to relocate the fetus back from the narrow birth canal and to reposition the legs or head into the correct position for delivery. In addition, rotational forces may be applied through the handle 41 to rotate the fetus if desired. The fetal repositioning technique may be used on live as well as dead fetuses.

Figure 8:
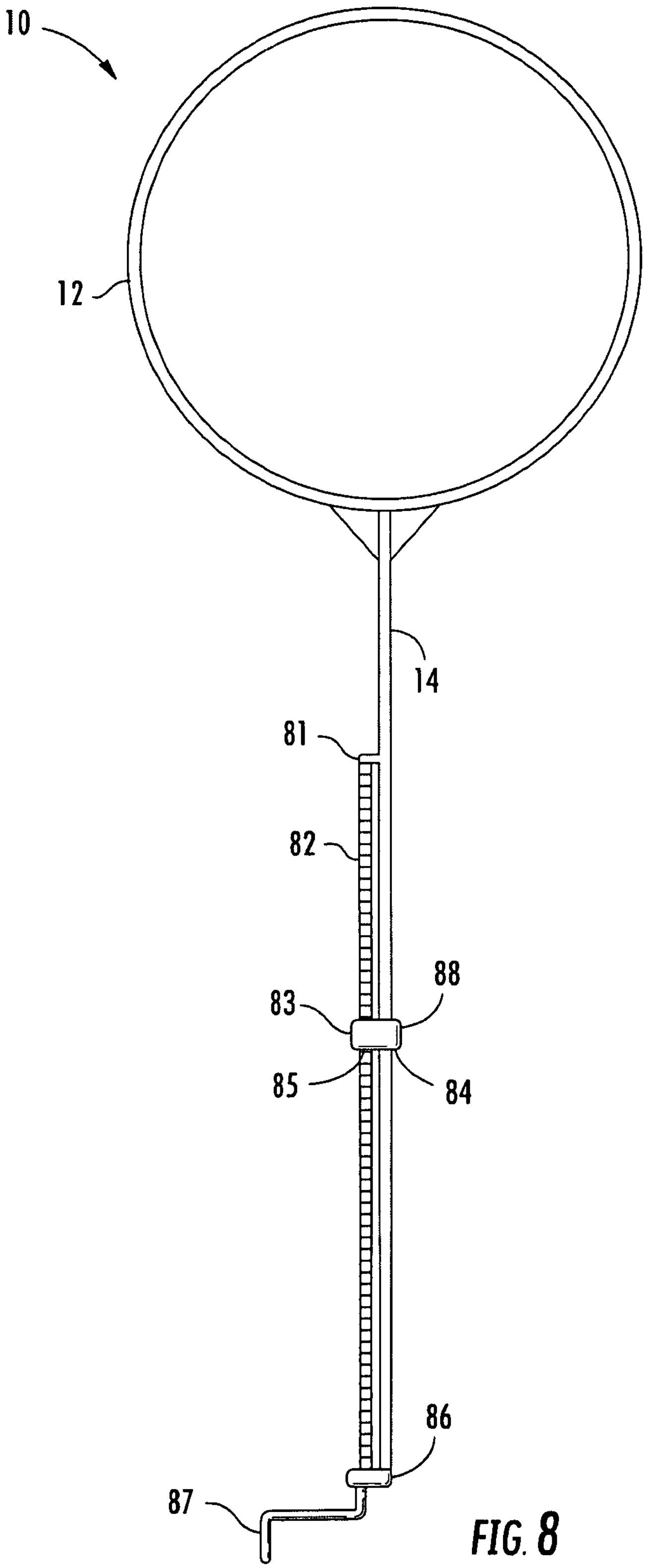
FIG. 8 substantially illustrates a fetotomy device with an alternative tensioning mechanism.

An alternative tensioning device is illustrated in FIG. 8. In this embodiment, the extension bar 14 of the device 10 is modified to include a stop 81. A threaded stem 82 runs parallel to the extension bar 14 and is maintained adjacent to the extension bar by a moveable shuttle 83. The shuttle has a hole 84 for slidably receiving the extension bar 14 and a threaded hole 85 for engaging with the threaded stem. A set of reduction gears 86 may be provided at the end of the extension bar 14 and threaded stem 82 such that the threaded stem is received between the gears 86 and the stop 81. The reduction gears 86 may receive a hand crank 87 or a motorized crank that causes the threaded stem to rotate. The shuttle 83 may include a hook 88 or similar attachment for receiving a secondary attachment device (not shown) as described above, such as a chain, that attaches to the fetal limb. In operation, the brace 12 is placed around the fetal limb and the secondary attachment device (not shown) is attached to the fetal limb. As the crank 87 is turned, the threaded stem 82 rotates, forcing the shuttle 83 to slide along the extension bar 14, thus increasing the distance between the shuttle 83 and the brace 12 and forcing separation of the fetal limb from the fetus. In one embodiment, the threaded stem may be made to turn by connection to a drill, such as a cordless hand drill.

The embodiments described above and illustrated in the drawings make specific reference to fetotomy of calf fetuses. However, the device and technique may be applied to other livestock and other mammals, including humans. In one example, the device may be used for performing fetotomy and/or fetal repositioning in zoological cases, with appropriate resizing of the device 10 where required.

Although the description above contains many specifications, these should not be construed as limiting the scope of the invention but as merely providing illustrations of some of the embodiments of this invention. Thus, the scope of the invention should be determined by the appended claims and their legal equivalents rather than by the examples given.

What is claimed is:

1. A method for performing a fetotomy, comprising:

(A) engaging a first portion of a fetal limb of a fetus with a brace, the brace comprising a rigid loop and an extension piece extending from the rigid loop;

(B) securing an attachment at a second portion of the fetal limb;

(C) performing a skin incision on the fetal limb;

(D) locating the rigid loop around the fetal limb and guiding the rigid loop and extension piece through a birth canal until the rigid loop engages a base of the fetal limb; and (E) providing tension between the brace and the attachment sufficient to separate the fetal limb from the fetus.

2. The method according to claim 1 wherein the first portion of the fetal limb is the base of the fetal limb.

3. The method according to claim 2 wherein providing tension comprises pushing at the base of the fetal limb using the brace and pulling on the fetal limb from the second portion of the fetal limb.

4. The method according to claim 1 wherein providing tension comprises operating a tensioning device.

5. The method according to claim 4 further comprising:

(A) connecting the brace at a first location of the tensioning device;

(B) connecting the attachment to a second location of the tensioning device; and (C) wherein providing tension comprises increasing a length between the first location and the second location.

6. The method according to claim 5 further comprising connecting the brace to the tensioning device via the extension piece, which comprises a coupler and coupling the extension piece to the tensioning device via the coupler.

* * * * *